United States Patent
Albers et al.

[11] Patent Number: 5,859,311
[45] Date of Patent: Jan. 12, 1999

[54] TRANSGENIC MICE WHICH OVEREXPRESS NEUROTROPHIN-3 (NT-3) AND METHODS OF USE

[75] Inventors: Kathryn M. Albers; Brian M. Davis, both of Lexington, Ky.

[73] Assignee: University of Kentucky Research Foundation, Lexington, Ky.

[21] Appl. No.: 534,685

[22] Filed: Nov. 27, 1995

[51] Int. Cl.$^6$ .............................. A61K 49/00; C12N 5/18; C12N 15/09; C12N 15/18

[52] U.S. Cl. ................................ 800/2; 424/9.1; 424/9.2; 435/172.3; 536/23.1; 536/23.51; 536/24.1

[58] Field of Search .................................. 800/2; 424/9.1, 424/9.2; 435/172.3; 536/23.1, 23.51, 24.1

[56] References Cited

U.S. PATENT DOCUMENTS

| | | | |
|---|---|---|---|
| 4,736,866 | 4/1988 | Leder et al. | 800/2 |
| 5,087,571 | 2/1992 | Leder et al. | 435/354 |
| 5,169,764 | 12/1992 | Shooter et al. | 435/69.7 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,180,820 | 1/1993 | Barde et al. | 536/23.51 |
| 5,210,026 | 5/1993 | Kovesdi et al. | 435/69.1 |
| 5,218,093 | 6/1993 | Guo et al. | 530/399 |
| 5,218,094 | 6/1993 | della Valle | 530/417 |
| 5,223,610 | 6/1993 | Burton et al. | 536/24.1 |
| 5,227,292 | 7/1993 | White et al. | 435/69.1 |
| 5,229,500 | 7/1993 | Barde et al. | 514/12 |
| 5,235,043 | 8/1993 | Collins et al. | 530/399 |
| 5,272,063 | 12/1993 | Chan et al. | 530/399 |
| 5,349,056 | 9/1994 | Panayotatos | 530/399 |
| 5,364,769 | 11/1994 | Rosenthal | 435/69.1 |
| 5,387,742 | 2/1995 | Cordell | 800/2 |

FOREIGN PATENT DOCUMENTS

| | | |
|---|---|---|
| WO91/02067 | 2/1991 | WIPO . |
| WO91/03568 | 3/1991 | WIPO . |
| WO91/03569 | 3/1991 | WIPO . |
| WO93/00909 | 1/1993 | WIPO . |

OTHER PUBLICATIONS

Vassar et al PNAS 86: 1563–1567, 1989.

Vassser, Robert, et al., "Tissue–specific and differentiation–specific expression of human K14 keratin gene in transgenic mice." Proc. Natl. Acad. Sci. USA, vol. 86, Mar. 1989, pp. 1563–1567.

Edwards, Robert H. et al., "Directed Expression of NGF to Pancreatic β cells in Transgenic Mice Leas to Selective Hyperinnervation of the Islets." Cell, vol. 58, Jul. 14, 1989, pp. 161–170.

Patil, N. et al., "Specific Neuronal Expression of Human NGF Receptors in the Basal Forebrain and Cerebellum of Transgenic Mice." Neuron, vol. 2, 1990, pp. 437–447.

Vassar, Robert et al., "Transgenic Mice Provide New Insights into the Role of TGF–α During Epidermal Development and Differentiation." Genes & Development, vol. 5, 1991, pp. 714–727.

Borrelli, Emiliana et al., "Pituitary Hyperplasia Induced by Ectopic Expression of Nerve Growth Factor." Proc. Natl. Acad. Sci. USA, vol. 89, Apr. 1992, pp. 2764–2768.

Ard, M.D. et al., "Cell Death During Development of the Cochlear and Vestibular Ganglia of the Chick." Intl. J. Dev. Neurosci., vol. 2, pp. 535–547, 1984.

Oppenheim, R.W., "Cell death during development of the nervous system." Ann. Rev. Neurosci., vol. 14, pp. 453–501, 1991.

Thoenen, H. et al., "Physiology of Nerve growth factor." Physiol. Rev., vol. 60, pp. 1284–1334, 1980.

(List continued on next page.)

*Primary Examiner*—Brian R. Stanton
*Attorney, Agent, or Firm*—McDermott, Will & Emery

[57] ABSTRACT

Transgenic mice express increased levels of neurotrophin-3 (NT-3) in epithelium when their ancestors are microinjected with the NT-3 gene. The NT-3 growth factor expressing transgenic mice are useful in the study of neurodegenerative disorders of the brain such as Parkinson's syndrome and Alzheimer's disease, of the spinal cord motor neurons such as amyotrophic lateral sclerosis, and for testing drug candidates for the treatment of these diseases.

7 Claims, 6 Drawing Sheets

OTHER PUBLICATIONS

Oppenheim, R.W., "The neurotrophic theory and naturally occuring motoneuron death." Trends In Neurosci., vol. 12, pp. 252–255, 1989.

Davies, A.M. et al., "Coordination of trophic interactions by separate developmental programs in sensory neurons and their target fields." J. Cell sci., vol. 15, pp. 111–116, 1991.

Oppenheim, R.W., "Neuronal cell death and some related regressive phenomena during neurogenesis." Studies in Dev. Biology, ed. W.M. Cowan, pp. 74–133, Oxford Univ. Press, 1981.

Cowan, W.M. et al., "Regressive events in Neurogenesis." Science, vol. 225, pp. 1258–1265, 1984.

Levi–Montalcini, R. et al., "Destruction of the sympathetic ganglia occurs in mammals exposed to an antiserum to an NGF." Proc. Natl. Acad. Sci. USA, vol. 46, pp. 384–391, 1960.

Hefti, F. et al., J. Neurosci., vol. 6, pp. 2155–2161, 1986.

Williams, L.R. et al., Proc. Natl. Acad. Sci. USA, vol. 83, pp. 9231–9235, 1986.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

CCAGCGGGAT CCGTGATGTC CATCTTGTTT TATGTG    3 6

( 2 ) INFORMATION FOR SEQ ID NO:2:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear

```
( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

CGGTACGGAT  CCGATGCCAA  TTCATGTTCT  TCCG                                              3 4
```

TRANSGENIC MICE WHICH OVEREXPRESS NEUROTROPHIN-3 (NT-3) AND METHODS OF USE

TECHNICAL FIELD

The present invention relates to transgenic mice that express increased levels of neurotrophin 3 (NT-3) in the epidermis and other stratified, keratinized epithelium. The transgenic mice have an altered peripheral nervous system showing rescued NT-3 responsive neurons from a programmed cell death that normally occurs in development. This is evidenced by an increase in the number of trk C receptor expressing sensory neurons in the phenotype of the transgenic mouse. In addition, K14-NT-3 mice have larger Merkel cell (touch dome) sensory units in the skin than controls. The NT-3 expressing transgenic mice of the present invention are valuable to researchers that study the role of NT-3 in the development and function of the central nervous system and peripheral nervous system.

BACKGROUND ART

Neurotrophin proteins support survival and differentiation of developing neurons. Target tissues such as skin produce limited amounts of neurotrophins during critical periods of development that act to rescue neurons from programmed cell death. Though target-derived influences of nerve growth factor (NGF) have been well documented, effects of other neurotrophins are less clear.

During development of the vertebrate nervous system up to half of all neurons generated undergo a process of naturally occurring cell death (See Ard, M. D., Morest, D. K. (1984),; Intl. J. Dev. Neurosci. 2, 535–547; and Oppenheim, R. W. (1991). Ann. Rev. Neurosci. 14, 453–501).

Neuronal death typically occurs shortly after neurons make functional connections within their target field. Survival during this period of innervation is thought to be dependent on the synthesis by the target tissue of a limited quantity of neurotropic substances. (See Thoenen, H. and Barde, Y. A. (1980), Physiol. Rev. 60, 1284–1334; Oppenheim, R. W. (1989), Trends in Neurosci. 12, 252–255; and Davies, A. M., Larmet, Y., Wright, E., Vogel, K. S. (1991), J. Cell Sci. 15, 111–116)).

The competition for target field-derived neurotrophic factors is thought to serve at least two functions: to ensure that an appropriate number of synaptic contacts are made at the target and to eliminate inappropriate neuronal projections. (See Oppenheim, R. W. (1981),. In Studies in Developmental Biology (ed. W. M. Cowan) p 74–133. Oxford University Press; and Cowan, W. M., Fawcett, J. W., O'Leary, D. D. M., and Stanfield, B. B. (1984), Science 225, 1258–1265)).

This concept is referred to as the neurotrophic hypothesis and predicts that the number of neurons in the adult could be increased if a higher concentration of neurotrophic factor(s) was available during the critical time when synaptic contacts are being established.

The NT-3 neurotrophin appears to have a role in neuron survival and maintenance. NT-3 is a member of the brain derived neurotrophic factor (BDNF)/nerve growth factor (NGF) neurotrophin-4 (NT-4) gene family. The development and maintenance of the nervous system depends on these proteins known as neurotrophic factors. Widespread neuronal cell death accompanies normal development of the central nervous system and peripheral nervous system, and plays a crucial role in regulating the number of neurons which project to a given target field (Berg, 1982, Neuronal Development, 397–331; Cowan et al., 1984, 225:1258–65).

Ablation and transplantation studies of peripheral target tissues during development have shown that neuronal cell death results from the competition among neurons for limiting amounts of survival factors (neurotrophic factors) produced in their projection fields. These observations led to the identification of nerve growth factor (NGF), which remains by far the best characterized neurotrophic molecule (Levi, Montalchini, and Angeletti, 1968, Physiol. Rev., 48:534–69; Thoenen and Barde, 1980, Rev. 60:1284–335).

Because NGF supports only a limited set of neuronal populations, the existence of additional neurotrophic factors has long been postulated (Varon, S. and Adler, R., 1981, Adv. Cellular Neurobiology, 2: 115–63; Barde et al., 1987, Prob. Brain Res., 71:185–9). While it is now clear that other neurotrophic factors exist, their extremely low abundance has impeded their molecular characterization. Nevertheless, purification of small amounts of two such proteins, namely brain derived neurotrophic factor and ciliary neurotrophic factor have recently permitted their cloning and sequencing (Leibrock et al., 1989, Nature, 341:149–52; Stockli et al., 1989, Nature, 342:21–28; and Lin et al., 1989, Science, 246:1023–25).

There have been numerous reports of neurotrophic factor activity in extracts of a great variety of tissues and in conditioned culture media of many different cell types. Progress in characterizing these activities and purifying the compounds has been hampered by the fact that such activities are present in extremely small amounts, the range of picograms and nanograms per gram of tissue.

Nerve growth factor (NGF) is a prototypical target-derived neurotrophic substance that has been shown to be essential for the survival and differentiation of neural crest-derived sensory neurons, sympathetic neurons, and forebrain cholinergic neurons. (See Levi-Montalcini, R. and Booker B. (1960), Proc. Natl. Acad. Sci. U.S.A 46, 384–391, and Hefti, F. (1986) J. Neurosci. 6, 2155–2161; Williams, L. R., Varon, S., Peterson, G., Wictorin, K., Fischer, W., Bjorklund, A. & Gage, F. H. (1986), Proc. Natl. Acad. Sci. U.S.A. 83, 9231–9235).

U.S. Pat. No. 5,180,820 to Barde et al. discloses nucleic acid sequences encoding brain derived neurotrophic factor of humans. U.S. Pat. No. 5,229,500 to Barde et al. claims pharmaceutical compositions including purified isolated nucleic acid sequences encoding brain derived neurotrophic factor.

U.S. Pat. No. 5,169,764 to Shooter et al. discloses and claims a nucleic acid molecule encoding a chimeric protein which has neurotrophic activity and consists of a chimeric protein including two neurotrophic factors selected from brain derived neurotrophic factor, ciliary neurotrophic factor, neurotrophin-3 and nerve growth factor.

U.S. Pat. No. 5,235,043 to Collins et al. discloses and claims a method for folding human mature nerve growth factor recombinantly expressed in E. coli wherein the protein maintains substantially full biological activity. U.S. Pat. No. 5,218,094 to de La Valle discloses a nominal neurotrophic factor isolated from mammalian brain tissue. U.S. Pat. No. 5,349,056 to Panayotatos discloses and claims a modified human ciliary neurotrophic factor. U.S. Pat. No. 5,364,769 to Rosenthal et al. discloses neurotrophic factor-4, isolated nucleotide sequences. U.S. Pat. No. 5,210,026 to Kovesdi et al. discloses human MK protein which is homologous to humor- and heparin-binding neurotrophic factor.

U.S. Pat. No. 5,272,063 to Chan et al. discloses and claims a method of producing biologically active mature human β-nerve growth factor in insect cells.

International Publication WO 91/03568 to Hyman et al. discloses a derived neurotrophic factor and claims recombinant DNA molecule comprising a nucleic acid sequence encoding brain derived neurotrophic factor.

International Publication 91/03569 to Hohn discloses neurotrophin-3. The publication claims a recombinant DNA molecule comprising a nucleic acid sequence encoding neurotrophin-3 or subsequences thereof. This international publication is incorporated herein by reference in its entirety.

Various transgenic mice have been patented. U.S. Pat. No. 4,736,866 to Leder et al. discloses a transgenic non-human eukaryotic animal whose germ cells and somatic cells contain an activated oncogene sequence introduced into the animal or an ancestor of the animal at an embryonic stage. The embryo of the mice were microinjected with approximately 500 copies of the RSV-S107 c-myc plasmid. The injected eggs were transferred to pseudopregnant foster mothers and allowed to develop to term. The plasmid contains a Rous Sarcoma Virus enhancer and promoter sequence. The resultant mice showed expression of the c-myc gene in the salivary gland, spleen, testes, lung, brain, and preputial gland and intestinal tissue.

U.S. Pat. No. 5,175,383 to Leder et al. discloses a male transgenic mouse containing germ cells and somatic cells which contain a recombinant gene which is a vertebrate gene in the Int-2/FGF family which is capable of promoting benign prostatic hyperplasia or hypertrophy. The fusion gene which is injected into the mouse embryonic tissue comprises a promoter sequence controlling transcription of the recombinant gene such as a promoter derived from the mouse mammary tumor virus and cytomegalovirus. The recombinant gene is preferably substantially homologous with (i.e., greater than 50% homologous in terms of encoded amino acid sequence) a naturally occurring, vertebrate gene in the Int-2/FGF gene family of murine growth factor encoding genes or their vertebrate counterparts, including the murine acidic or basic fibroblast growth factor genes, the murine FGF-5 gene, the murine epidermal growth factor gene, the murine insulin-like growth factor-1 and -2 gene, the murine α-transforming growth factor gene with a murine hst/KS3 gene. The transgenic mice of Leder et al. exhibit prostate hyperplasia and give sterile offspring.

U.S. Pat. No. 5,087,571 to Leder et al. discloses a non-human eukaryotic animal whose germ cells and somatic cells contain an activated oncogene. The embryo of the mice were microinjected with approximately 500 copies of the RSV-S107 c-myc plasmid. The injected eggs were transferred to pseudopregnant foster mothers and allowed to develop to term. The plasmid contains a Rous Sarcoma Virus enhancer and promoter sequence. The resultant mice showed expression of the c-myc gene in the salivary gland, spleen, testes, lung, brain, and preputial gland and intestinal tissue.

U.S. Pat. No. 5,175,384 to Krimpenfort et al. discloses transgenic mice having a phenotype characterized by the substantial absence of mature T-lymphocytes. The mouse is produced by introducing a transgene into a zygote of a mouse which comprises gene fragment which encodes a T-cell antigen receptor polypeptide variant which is incapable of mediating T-cell maturation in the transgenic mouse.

U.S. Pat. No. 5,175,385 to Wagner et al. discloses the production of a transgenic mouse with enhanced viral resistance which is transmissible to its offspring. The transgenic mouse is prepared by introduction of a gene encoding a human interferon having anti-viral activity into a host mouse. The plasmid of Wagner et al. contains a methallothionein-1 promoter and the genomic human beta interferon gene. When these mice were injected with pseudorabies virus they showed an increased resistance to the virus and although many mice died they died considerably later than did the control animals.

Vassar et al., in the *Proceedings of the National Academy of Sciences*, Volume 86, pages 1563–1567, March 1989, disclose "Tissue-specific and Differentiation-specific Expression of a Human K14 Keratin Gene in Transgenic Mice". This publication discloses that Vassar et al. used a plasmid containing a K14 keratin promoter and a K14 keratin gene sequence tagged with a sequence from the neuropeptide substance P and determined the expression of the plasmid and K14 keratin tagged substance P in the skin of transgenic mice.

Vassar et al. in *Gene & Development*, Volume 5, pages 714–727, (1991) disclose "Transgenic Mice Provide New Insights into the Role of TGF-α During Epidermal Development and Differentiation". This publication discloses the construction of transgenic mice using a plasmid which contains the K14 keratin promoter and the TGF-α gene. Vassar et al. disclose that the TGF-α gene belongs to the epidermal growth factor family of proteins and shows structural homology with the epidermal growth factor. These transgenic mice showed gross phenotypic abnormalities in their skin including flaky outer epidermal layers with stunted hair growth and wrinkling. The plasmid used to create this transgenic mouse also included human growth hormone fusion gene.

U.S. Pat. No. 5,387,742 discloses transgenic mice which exhibit amyloid brain deposits characteristic of Alzheimer's disease.

PCT Publication WO 93/00909 is directed to a method of treating neurotrophin-expressing tumors by administering a sequence complementary to at least a portion of a RNA transcript of brain-derived neurotrophic factor gene.

Heretofore there has been no convenient method to investigate how neurotrophic factors such as NT-3, affect neuron survival and development of the peripheral nervous system or provide a practical model for testing drug candidates for the treatment of neurodegenerative disorders of the brain such as Parkinson's syndrome and Alzheimer's disease and assessing the effect of drug candidates on the central nervous system (CNS) and peripheral nervous system (PNS).

The present invention overcomes the deficiency by providing transgenic mice which express increased levels of Neurotrophin-3 in the epidermis and other stratified, keratinized epithelium. The transgene DNA construct injected into the mouse embryos contain a human K14 keratin promoter and enhancer region linked to the coding sequences of mouse Neurotrophin-3 gene. The mice can be used to study the role of NT-3 in supporting neuronal survival and in neurodegenerative disorders of the CNS and PNS.

SUMMARY OF THE INVENTION

The invention provides a transgenic mouse whose somatic and germ cells contain and express a gene encoding for NT-3. The gene was introduced into a mouse or an ancestor of the mouse at an embryonic stage. The NT-3 gene is operatively linked to a human K14 keratin promoter and enhancer region. The increased expression of the transgene was achieved by adding a region from the human growth hormone gene at the 3' end of the construct. The NT-3 in transgenic mice appears to alter the peripheral nervous system by rescuing NT-3 responsive neurons from a programmed cell death that normally occurs in development. NT-3 transgenic mice appear to have more nerve terminals in the skin, particularly in association with hairs and touch dome mechanoreceptor endings.

The invention also provides for a mouse wherein the NT-3 gene has been introduced into an ancestor of said mouse at an embryonic stage by microinjection. In an additional embodiment, the mouse NT-3 gene is further operatively linked to the human growth hormone gene.

The invention provides for a mouse which has a phenotype characterized by an altered peripheral nervous system showing rescued NT-3 responsive neurons from a programmed cell death that normally occurs in development. This is evidenced by an increase in the number of trk C receptor expressing sensory neurons in the phenotype of the transgenic mouse. In addition, K14-NT-3 mice have larger Merkel cell (touch dome) sensory units in the skin than controls.

Advantageously, the present invention provides a method of producing the transgenic mouse which overexpresses NT-3 which comprises (a) providing a mouse NT-3 gene operatively linked to a human K14 keratin promoter and enhancer region functional in said mouse;

(b) introducing said gene into a mouse embryo;

(c) transplanting said embryo into a pseudopregnant mouse; and (d) allowing said embryo to develop to term.

Furthermore, the invention provides a method of testing the efficacy of drugs in treating neurodegenerative disorders comprising administering said drug to a mouse according to the invention, and determining the behavioral effects and tissue changes of said drug on said mouse.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF DRAWINGS

FIGS. 1A–1D show isolation and expression of the K14-NT-3 transgene in transgenic mice. 1(A) shows the NT-3 DNA was ligated into the BamH1 site of the K14-hGH cassette vector and purified. 1(B) shows founder offspring were screened and transgene copy estimated by film densitometry from slot blots on which 2 μg of denatured tail DNA was bound by baking to Nytran membrane and hybridized with a $^{32}$P-labeled probe to the NT-3 sequence. 1(C) shows transgene expression was measured by Northern analysis of RNA isolated from shaved back skin. 1(D) shows in situ hybridization using a $^{35}$S-labeled antisense probe made against the NT-3 mRNA confirmed K14-NT-3 transgene expression in basal keratinocytes of the epidermis (left panel, control tail skin; right panel, transgenic tail skin).

FIGS. 2A–2F show histological and immunocytochemical analysis of transgenic skin. Flank skin from control (A) and transgenic (B) mice was hematoxylin and eosin stained. Note increased size of touch dome (bracketed area) and increased cellularity beneath touch dome in transgenic sample. Innervation to the skin and touch domes was visualized by immunolabeling tissue sections using anti-PGP9.5 (Ultraclone) (FIGS. 2C, 2D) and anti-NF150 (Chemicon) (FIGS. 2E, 2F) antibodies. PGP9.5 immunoreactivity was more extensive overall in transgenic skin (FIG. 2D) compared to control (FIG. 2C), particularly in areas surrounding hair follicles. Touch domes of NT-3 mice (FIG. 2F) were larger and appeared to have greater innervation density than control touch domes (FIG. 2E).

STATEMENT OF DEPOSIT

The plasmids used to transform the mice of the present invention have been deposited under the terms of the Budapest Treaty with the American Type Culture Collection, 12301 Parklawn Dr. Rockville, Md. 20852. The K14 NT-3 hGH plasmid in E. coli has ATCC Accession No. 69889 and was received Aug. 16, 1995.

During the pendency of this application, access to the deposit will be forwarded to one determined by the Commissioner to be entitled thereto; (b) all restrictions imposed by the depositor on the availability to the public of the deposited material will be irrevocably removed upon the granting of the patent, (c) the deposit will be maintained for a period of at least thirty years or at least five years after the most recent request for the furnishings of a sample of the deposited material, (d) the deposit will be replaced should it become necessary due to inviability, contamination or loss of capability to function in the manner described in the specification.

DETAILED DESCRIPTION OF THE INVENTION

To examine target-derived effects of neurotrophin-3 (NT-3), transgenic mice were isolated that overexpress NT-3 in the epidermis. Experiments that examine the neuroanatomical and neurochemical changes induced by NT-3 expression in skin are conducted. Neurons of the trigeminal, superior cervical, and dorsal root ganglia are examined. Behavioral testing is initiated to determine whether alteration in sensory perception is induced by the increased neuronal innervation. Transplantation studies examine the usefulness of the transgenic skin in supplying NT-3 to neuronal lesion sites.

It was discovered that the production of NT-3 in transgenic mice alters the peripheral nervous system by rescuing NT-3 responsive neurons from a programmed cell death that normally occurs in development. This is evidenced by an increase in the number of trk C receptor expressing sensory neurons.

In addition, K14-NT-3 mice have larger Merkel cell (touch dome) sensory units in the skin than controls. These mice can be used in conjunction with K14-NGF and K14-

BDNF transgenic mice to examine the role and possible use of neurotrophic compounds in controlling the development and function of the nervous system.

Neurotrophins are growth factors that have profound effects on the development and function of the mammalian nervous system. Transgenic mice were isolated that express increased levels of NT-3 in the epidermis and other stratified, keratinized epithelium. The transgene DNA construct injected into mouse embryos contains the human K14 keratin promoter and enhancer region linked to the coding sequences of the mouse NT-3 gene (FIG. 1). To increase expression of the transgene, a region from the human growth hormone gene was added at the 3' end of the construct. Eleven founder mice were isolated; three lines were developed for further use.

The results support the neurotrophic hypothesis and specifically demonstrate that the skin, by regulating the timing and amount of neurotrophin expression independent of innervation plays a central role in the development of the peripheral nervous system.

Elevated levels of NT-3 in the mice of the invention were found to increase the size of touch dome units, the number of Merkel cells (MC) per unit, and their level of neuronal innervation. In addition, the number of myelinated and unmyelinated axons in cutaneous nerves was increased approximately 60% while the number of trkC expressing neurons in the trigeminal ganglia doubled.

Previous studies of transgenic mice that overexpress NGF in the skin showed a dramatic increase in innervation density, an increase in the number of trkA expressing neurons, and an overall hypertrophy of the peripheral nervous system (1, 2). Because skin also synthesizes the neurotrophins NT-3, BDNF, and NT-4 during critical periods of sensory neuron development (3, 4, 5), we developed additional lines of neurotrophin expressing mice.

Figure 1A:
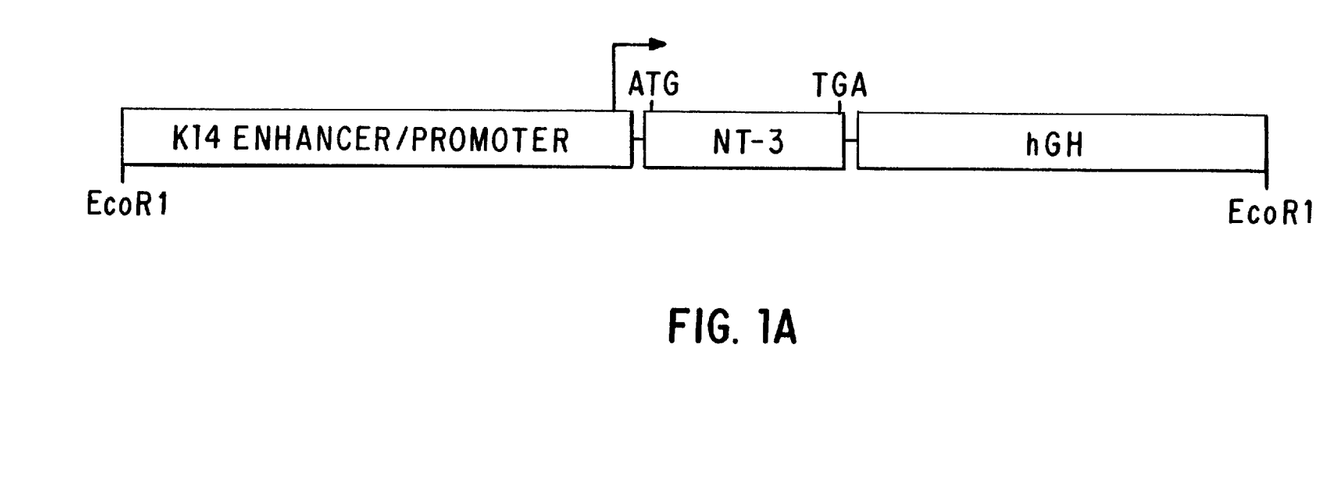
Figure 1B:
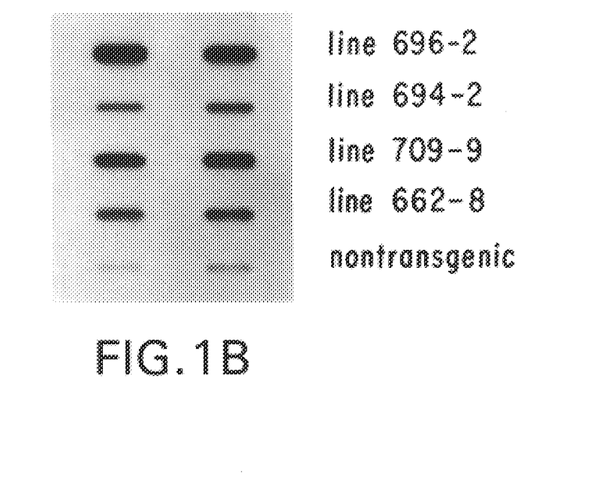
Figure 1C:
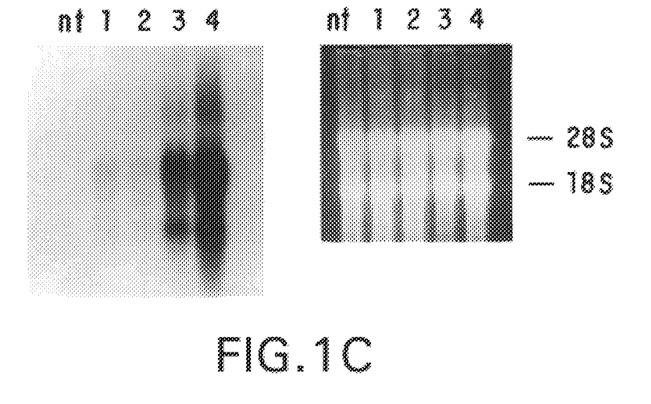
Figure 1D:
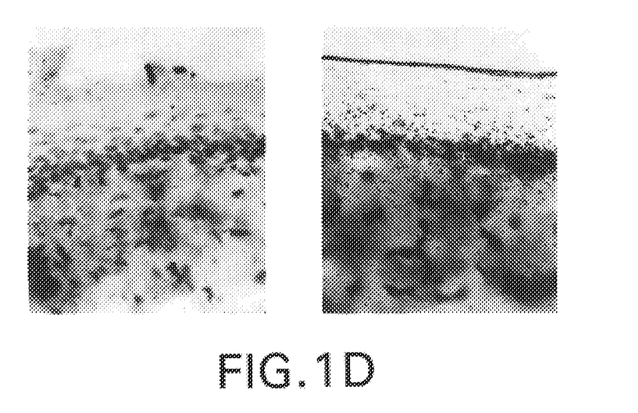

The transgenic mice of the invention overexpress NT-3 in the epidermis. The expression of NT-3 by the skin suggests that it may, like NGF, support distinct subsets of cutaneous sensory neurons and thereby influence development of innervation density and sensory responsiveness (1, 6, 7, 8). NT-3 gene expression is detectable in developing skin at embryonic day 9.5 (E9.5), peaks at E13, and then declines to lower adult levels (9). To increase levels of target-derived NT-3, transgenic mice were isolated that overexpress NT-3 in basal keratinocytes of the epidermis using promoter and enhancer sequences of the human keratin K14 gene (1, 10) (FIG. 1a). Expression of K14 in developing epidermis is initiated by approximately day 14 and continues in the adult. The onset of transgene expression, therefore, overlaps with the normal decline of NT-3 expression in the skin. Heterozygote transgenic offspring from K14-NT-3 founder mice (FIG. 1B) appeared normal. They were characterized for transgene mRNA expression using Northern analysis of RNA isolated from back skin (FIG. 1C) and in situ hybridization analysis of tail skin (FIG. 1D). Two lines (696-2 and 694-2) that expressed the highest levels of the K14-NT-3 transcript were used for this study.

Figure 2A:
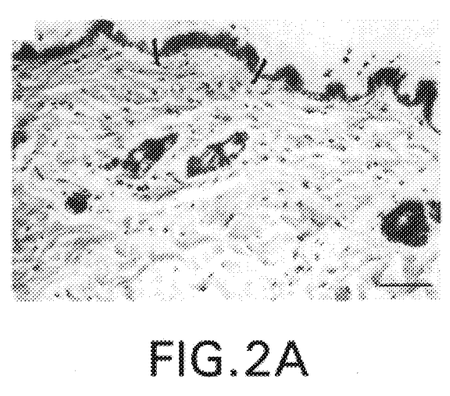
Figure 2B:
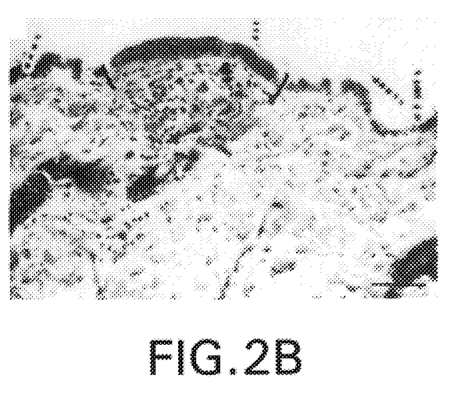

Histological examination of transgenic skin showed a remarkable increase in the size of touch domes (FIG. 2A, B), mechanoreceptor units innervated by large diameter, slowly adapting type I (SAI) sensory neurons (11). Touch domes of transgenic mice (FIG. 2B) were nearly doubled in size compared to controls (FIG. 2A). In dermis beneath touch domes an increased cellularity was consistently observed and appears to represent Schwann cells associated with the innervating fibers. An increased labeling density in this region with an antibody that recognizes a galactocerebroside component of myelin protein expressed in Schwann cells (01 antibody) is noted.

Figure 2C:
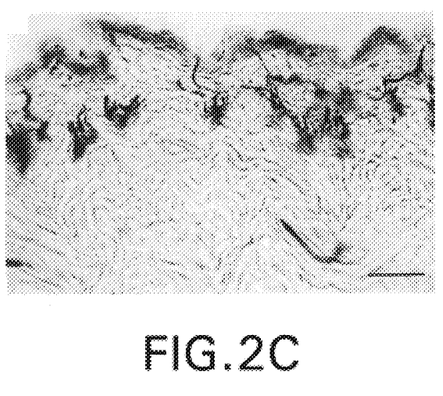
Figure 2D:
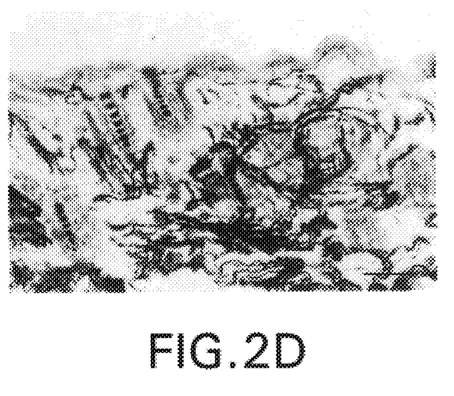
Figure 2E:
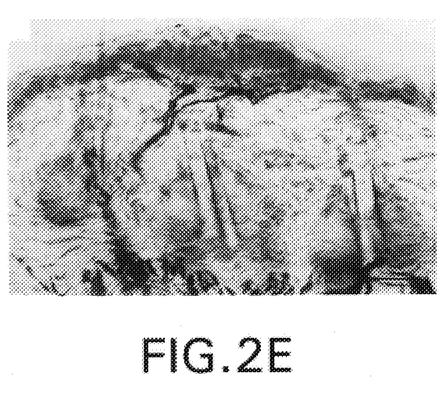
Figure 2F:
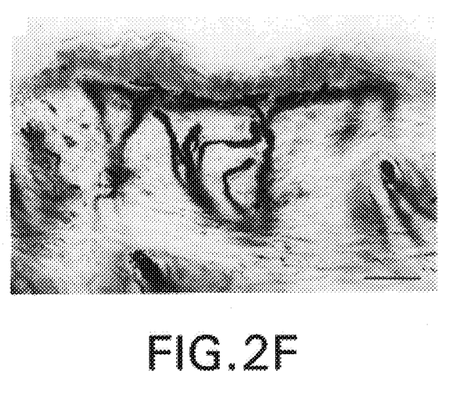

To examine the nature of innervation to touch dome units, sections of control and transgenic skin were immunolabeled using an antibody against protein PGP 9.5 (FIG. 2C, D), which recognizes all neuronal fiber types, and an antibody against neurofilament 150 (NF 150; FIG. 2E, 2F), a protein primarily localized to myelinated axons. An increase in the density of innervation to the skin and touch dome units of the transgenic mice (FIG. 2C, 2D) appeared in large part attributable to increased projection of afferents to hair follicles, particularly in regions where circular endings were located. Given the physiologically measured decrease in D-hair units in skin of NT-3 (+/−) mutant mice (12), this increase shows that these circular endings may represent the anatomical substrate of the D-hair unit. The clearly larger touch dome units of transgenics were also innervated by an increased number of immunoreactive fibers (FIG. 2F) compared to controls (FIG. 2E), suggesting that the transgenic touch domes are enhanced functionally as well.

Figure 3A:
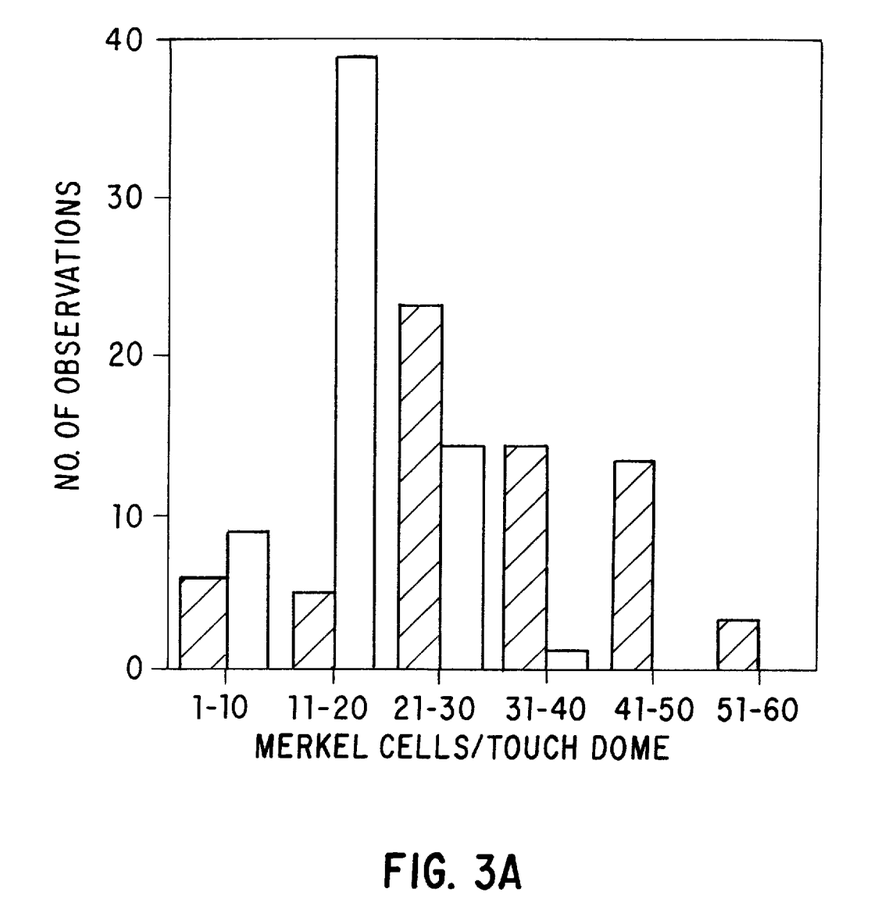
FIGS. 3A–3B show transgene expression of NT-3 increases the number of Merkel cells and cutaneous myelinated nerves. Histogram 3(A) illustrates the number of MCs per touch dome unit shows increased numbers of MCs associated with the larger touch dome areas in the NT-3 transgenic skin. 3(B) left side shows cross section of saphenous nerve of control mouse; right side is nerve from an NT-3 transgenic. Axon counts of this cutaneous nerve show a 60% increase in the number of myelinated and unmyelinated fibers.

SAI afferents innervating touch domes terminate on specialized neuroendocrine cells known as Merkel cells (MCs). MCs are located at the epidermal-dermal junction and are thought to act as transducers of mechanical deformation (13). To determine whether MC numbers were increased in conjunction with the increase in touch dome area and innervation, control and transgenic mice were injected with quinacrine fluorescent dye, a compound selectively concentrated in neuroendocrine cell types (14). Counts of quinacrine labeled control and transgenic skin showed a statistically significant ($p<0.001$) increase in the number of MCs per touch dome in the NT-3 transgenics (FIG. 3A).

Gene knockout and cell culture studies have shown NT-3 supports the survival of myelinated sensory neurons of large axonal caliber (15, 16). To examine whether overexpression of NT-3 affected cutaneous myelinated nerves, we measured the number of myelinated fibers in control and transgenic mice by counting cross-sectional profiles of the saphenous cutaneous nerve (ie. 3B). Axon counts from control (521±6.8 s.e.m.) and transgenic 839±11.8 s.e.m.) mice showed transgenic nerves to have an approximate 60% increase in the number of myelinated fibers (($p<0.001$) compared to controls). This increase in axon count was reflected by the near doubling of the transgenic saphenous nerve cross-sectional area (FIG. 3B, right side) compared to the control nerve (FIG. 3B, left side) (34,016 units $\mu m^2$ compared to 17,196 $\mu m^2$, $p<0.001$). Subsequent counting of unmyelinated axons showed there number to also be increased by 60%.

The biological effects of neurotrophins are primarily mediated through the trk family of tyrosine protein kinases (17, 18, 19). TrkA preferentially binds NGF, trkB binds BDNF and NT-4, and trkC binds NT-3. Approximately 10% of dorsal root ganglia (DRG) sensory neurons express the trkC receptor, 10% express the trkB receptor, whereas 40% express trkA (20, 21, 22, 23).

Target production of neurotrophins affects neuron survival and differentiation via a trk receptor mediated uptake process that facilitates internalization and retrograde transport to the soma (24). Abundant evidence supports this mechanism for the prototypical neurotrophin NGF and its high affinity receptor trkA. Mice lacking a functional NGF gene lack trkA expressing neurons (8), whereas mice that overexpress NGF have an increased number of trkA expressing neurons (2).

To examine whether increased expression of NT-3 acted to increase the number of sensory neurons that expressed trkC, in situ hybridization was carried out using a radiolabeled probe to the trkC receptor mRNA (25). Trigeminal ganglia from the 694-2 and 696-2 transgenic lines had an approximate two-fold increase in the number of trkC expressing neurons compared to control ganglia (Table 1). Interestingly, a plot of these values versus animal age (FIG. 4) revealed that, for both control and transgenic mice, the number of the trkC positive neurons accumulated with age, stabilizing by approximately three weeks. This increase in trkC neurons may reflect a maturation and/or refinement of the sensory system during the early weeks of development and demonstrates the plasticity inherent in the peripheral sensory system.

Studies of NT-3 and trkC gene knockout mice showed a depletion of proprioceptive 1A afferents as well as the muscle spindle sensory end organs they innervate (15, 16, 26). The disappearance of proprioceptive neurons cannot, however, account for the overall 50% loss of sensory neurons in the DRG of NT-3 (−/−) animals and suggests other sensory neurons are dependent on NT-3 for their development and maintenance.

Figure 4:
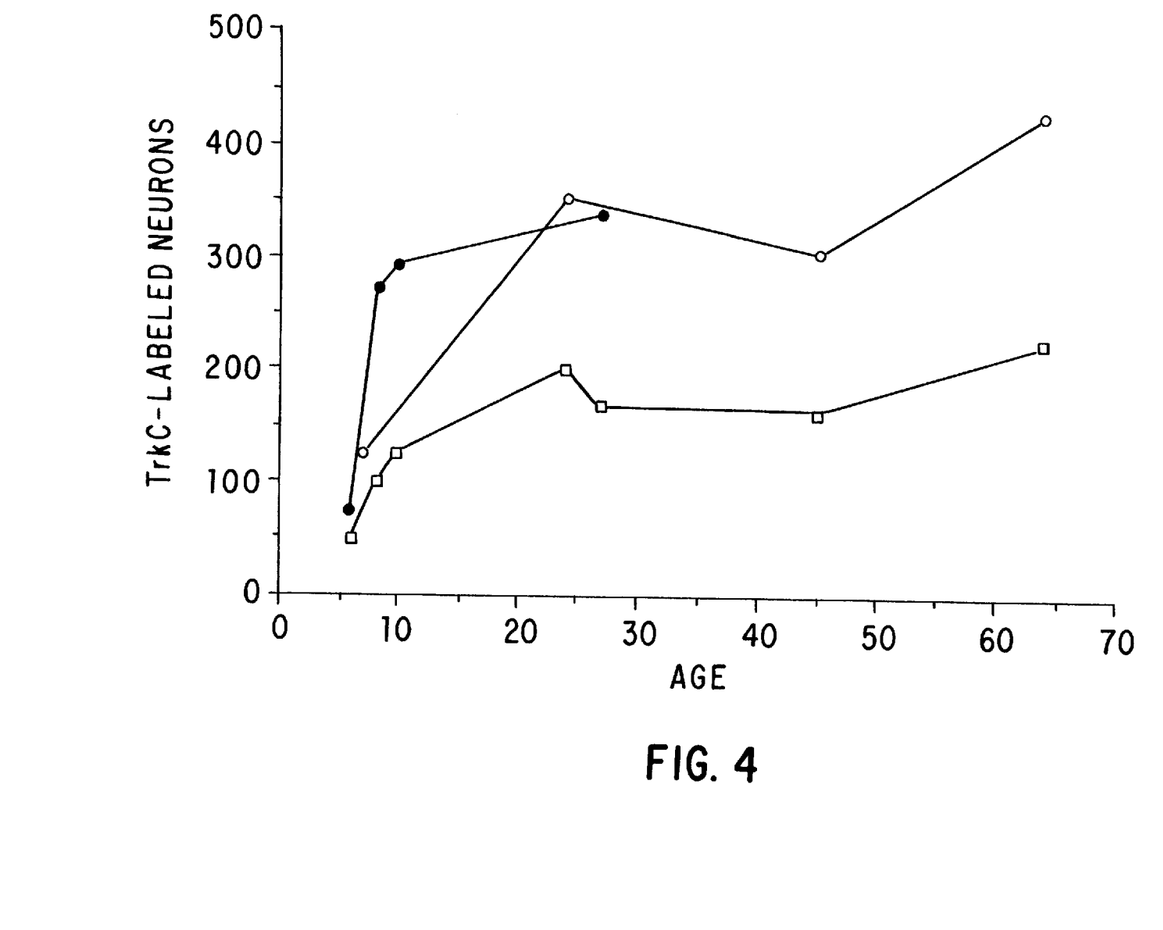
FIG. 4 shows enhanced expression of NT-3 increases the number of trkc expressing sensory neurons.

The present studies identify cutaneous touch dome complexes and their associated MCs as another sensory end organ responsive to NT-3 and, by supposition, innervated by trkC receptor expressing neurons. This observation is supported by the additional innervation to touch dome units, the increase in MCs, and the increase in trkC expressing neurons in the sensory ganglia (FIG. 4).

The enlargement of touch domes and number of MCs may result from the enhanced innervation by SA1 afferents generated by the increased level of NT-3. In support of this mechanism, studies by Nurse et al., (27) showed that denervation of backskin of rats led to a decline in the number of MCs, i.e., the sensory nerve supply was required for MC maintenance. In addition, MCs are depleted in NT-3 (+/−) mice which lack SA1 type fibers (12).

In the present model an overabundance of appropriate SA1 fiber types appear available to contact MCs and, interestingly, this overabundance enhances the development of the end organ. Effects of the epidermally expressed NT-3 on the cells comprising the touch dome is another possible factor in touch dome development, perhaps acting in a synergistic manner with the afferent innervation.

Table 1. Number of TrkC receptor expressing neurons in the trigeminal ganglion of control and K14-NT-3 transgenic mice. Positive cells were counted in every tenth section of serial sectioned ganglia. Transgenic and control ganglia were hybridized together and therefore exposed to the same conditions.

TABLE 1

| Sample | Age (weeks) | TrkC labeled neurons (avg) |
|---|---|---|
| Transgenic line 696–2 | 5 (n = 2) | 62 |
|  | 7 (n = 1) | 259 |
|  | 9 (n = 2) | 283 |
|  | 26 (n = 1) | 327 |
| Transgenic line 694–2 | 6 (n = 4) | 113 |
|  | 23 (n = 2) | 342 |
|  | 44 (n = 1) | 294 |
| Controls | 63 (n = 2) | 417 |
|  | 5 (n = 2) | 37 |
|  | 7 (n = 2) | 90 |
|  | 9 (n = 1) | 116 |

TABLE 1-continued

| Sample | Age (weeks) | TrkC labeled neurons (avg) |
|---|---|---|
|  | 23 (n = 1) | 189 |
|  | 26 (n = 1) | 158 |
|  | 44 (n = 2) | 156 |
|  | 63 (n = 1) | 214 |

To correct for variation in neuron size, recursive translation analysis was performed on labeled neuron cell counts. The perimeter (p) of labeled neuronal profiles were drawn by camera lucida and the cross sectional area (A) of each profile calculated from a digitized image of the drawing. The radius (r) of each profile was approximated using r=square root of (A/p). The frequency histogram of the profile radii was transformed to an estimate of the true frequency histogram of neuronal radii with a computer program developed by Rose and Rohrlich (30). Summing the frequencies in all bins of the resulting histogram gives an estimate of cell number in one section of a ganglion. The recursive translation method was repeated on equally spaced 20 μm serial sections (for example, on every $n^{th}$ section) throughout the entire ganglion. Summing the number of cells across all of the sampled sections and multiplying the total by n gives an unbiased estimate of the true number of labeled cells. n equals the number of mice used per age group.

DETAILED DESCRIPTION OF DRAWINGS

FIG. 1 shows isolation and expression of the K14-NT-3 transgene in transgenic mice. Mouse NT-3 cDNA was cloned by PCR amplification of DNA isolated from tail using primers (5'CCAGCG GGATCCGTGATGTCCATCTTGTTTTATGTG 3' (SEQ ID NO:1) and 5'CGGTAC GGATCCGATGCCAATTCATGTTCTTCCG 3' (SEQ ID NO:2)) that amplified the DNA sequence encoding amino acids −140 to +124 according to the numbering of Yancopoulos et al., (28). This region contains the putative signal peptide (−140 to −1), the mature peptide (+1 to +119), and the NT-3 stop codon (+120). To facilitate cloning, primers contained a BamH1 recognition sequence (underlined in sequence). DNA sequencing showed a nucleotide change in the cloned sequence that resulted in a conservative amino acid change (ala→val) at amino acid residue [−9]. 1(A) shows the NT-3 DNA was ligated into the BamH1 site of the K14-hGH cassette vector (10) and purified as described in (1). The K14-NT-3 sequence was microinjected into pronuclei of B6×C3 F1 hybrid mouse embryos and implanted into pseudopregnant females using standard procedures (29).

Four founder mice (696-2, 694-2, 709-9, and 662-8) were identified by Southern hybridization using a random primed $^{32}$P-dCTP labeled probe made to the full length NT-3 cDNA. 1(B) shows founder offspring were screened and transgene copy estimated by film densitometry from slot blots on which 2 μg of denatured tail DNA was bound by baking to Nytran membrane and hybridized with a $^{32}$p-labeled probe to the NT-3 sequence. Copy number estimates were 8 (line 696-2), 2 (line 694-2), 5 (line 709-9), and 3 (line 62-8).

Because of poor reproductive yields of homozygous mice, experimental analyses were restricted to hemizygous transgenics. 1(C) shows transgene expression was measured by Northern analysis of RNA isolated from shaved back skin. RNA was purified using Trizol reagent (Gibco-BRL) according to the manufacturers protocol. 10 μg of RNA was resolved on a 1.2% agarose formaldehyde denaturing gel, transferred to Nytran membrane, baked at 80° C., and hybridized at 65° C. in the presence of 50% formamide to a $^{32}$P-CTP labeled riboprobe made to the full length NT-3 sequence. Membranes were hybridized overnight, washed, and exposed to X-ray film. Lane nt, nontransgenic RNA; lane 2, 662-8 RNA; land 3, 709-9 RNA; land 3, 694-2 RNA, and land 4, 696-2 RNA. 1(D) shows In Situ hybridization using a $^{35}$S-labeled antisense probe made against the NT-3 mRNA confirmed K14-NT-3 transgene expression in basal keratinocytes of the epidermis (left panel, control tail skin; right panel, transgenic tail skin). Conditions of probe hybridization were as described in (1).

FIG. 2 shows histological and immunocytochemical analysis of transgenic skin. Flank skin from control (A) and transgenic (B) mice was hematoxylin and eosin stained. Note increased size of touch dome (bracketed area) and increased cellularity beneath touch dome in transgenic sample. Innervation to the skin and touch domes was visualized by immunolabeling tissue sections using anti-PGP9.5 (Ultraclone) (FIG. 2C, 2D) and anti-NF150 (Chemicon) (FIG. 2E, 2F) antibodies. PGP9.5 immunoreactivity was more extensive overall in transgenic skin (FIG. 2D) compared to control (FIG. 2C), particularly in areas surrounding hair follicles.

Touch domes of NT-3 mice (FIG. 2F) were larger and appeared to have greater innervation density than control touch domes (FIG. 2E). Immunolabeling was done on 30 μm thick floating sections that were blocked in 5% normal goad serum (NGS), 2% bovine serum albumin (SA), and 0.25% triton X-100 made in tris buffered saline for 1 h, exposed overnight at room temperature to diluted antibodies (anti-PGP 9.5, 1:500 dilution of biotinylated goat anti-rabbit secondary for 1 h followed by a strepavidin complex incubation (Vector Labs)). Binding was visualized using a nickel cobalt enhanced diaminobenzidine reaction. Scale bars A–d, 50 μm; E–F, 100 μm.

Figure 3B:
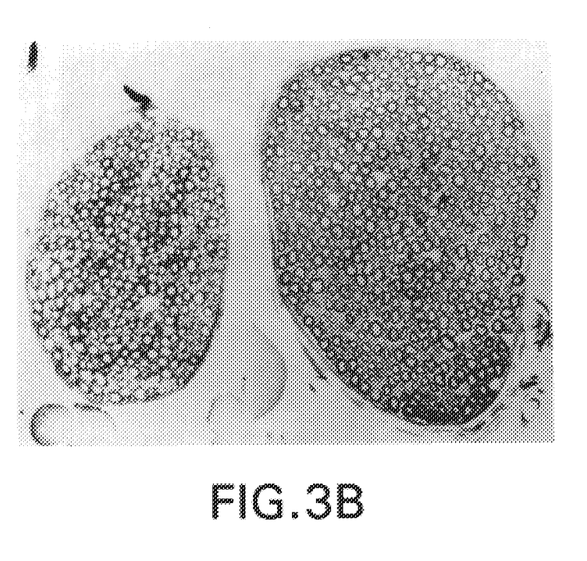

FIG. 3 shows transgene expression of NT-3 increases the number of Merkel cells and cutaneous myelinated nerves. Histogram 3(A) illustrating the number of MCs per touch dome unit shows increased numbers of MCs associated with the larger touch dome areas in the NT-3 transgenic skin. Numbers were determined for 3 transgenic and 3 controls by counting quinacrine hydrochloride labeled cells on full thickness skin sections using a microscope equipped with FITC fluorescent optics (14). Back skin of adult mice was depilated and 24 h later mice were injected intraperitoneally (15 mg/kg) with quinacrine solution made in phosphate buffered saline. 20 h later mice were deeply anesthetized and back skin removed and analyzed. 3(B) shows on the left side a cross section of saphenous nerve of control mouse; right side is nerve from an NT-3 transgenic. Saphenous nerves of transgenics were nearly double in size compared to control nerves and had a 40% increase in the number of myelinated axons. Nerve samples were collected from transgenic (n=3) and control (n=3) mice deeply anesthetized with Avertin and perfused intracardially with a solution of 2% paraformaldehyde and 2% glutaraldehyde made in phosphate buffer. Tissues were fixed overnight, embedded in epon, thin sectioned, stained with toluidine blue, and myelinated profiles counted with the aid of a computer. Nerve counts and MC counts were analyzed from the same mice.

FIG. 4 shows enhanced expression of NT-3 increases the number of trkC expressing sensory neurons. To identify trkC neurons in trigeminal ganglia in situ hybridization was performed using a $^{35}$S-labeled antisense probe made against rat trkC mRNA (25). Values at timepoints listed in Table 1 were plotted against age and show an overall increase of trkC neurons for both transgenic lines compared to controls and reveal a significant positive correlation between the number of trkC neurons and age for both transgenic (line 694-2, r=0.626 p<0.05) and control (r=0.802; p<0.005) mice. Control (-"box"-); line 696-2 (-"dark circle"-); line 694-2 (-o).

TABLE 2

| Mouse Number | Phenotype | Number of trk C Labeled neurons | |
|---|---|---|---|
| 711-2 | Nontransgenic | 272 | |
| 696-2F1-25 | Nontransgenic | 292 | Average value |
| 696-2NT14 | Nontransgenic | 136 | for nontransgenic |
| 696-2NT17 | Nontransgenic | 208 | mice = 227 |
| 696-2F2-6 | Transgenic | 758 | |
| 694-2 | Transgenic | 645 | Average value |
| 696-2F2-30 | Transgenic | 515 | for transgenic |
| 696-2F2-27 | Transgenic | 649 | mice = 642 |

EXAMPLE 1

Construction of K14-NT-3 transgene and introduction into mice. Transgenic mice that overexpress NT-3 in the skin were generated by linking a PCR cloned NT-3 cDNA downstream of 2 Kbp of the human D14 keratin promoter and enhancer sequence. NT-3 cDNA was cloned by PCR amplification of DNA isolated from tail using primers ( 5 ' C C A G C G <u>GGATCC</u>GTGATGTCCATCTTGTTTTATGTG 3' (SEQ ID NO:1) and 5'CGGTAC <u>GGATCC</u>GATGCCAATTCATGTTCTTCCG 3' (SEQ ID NO:2)) that amplified the DNA sequence encoding amino acids −140 to +124 according to the numbering of Yancopoulos et al. This region contains the putative signal peptide (−140 to −1), the mature peptide (+1 to +119), and the NT-3 stop codon (+120). To facilitate cloning primers were generated to contain a BamH1 recognition sequence (underlined in primer sequence). Sequencing of the cloned NT-3 showed a nucleotide change that resulted in a conservative amino acid change (ala→val) in the signal peptide region at amino acid residue [−9]. To construct the K14-NT-3-hGH transgene the NT-3 cDNA was ligated into the BamH1 site of the K14-hGH cassette vector (Vassar and Fuchs, 1991, supra). Dr. Elaine Fuchs (University of Chicago) provided the K14-hGH plasmid.

K14-hGH contains 2.1 kbp of 5' upstream sequence of the human K14 keratin gene and a 1.8 kbp intron containing sequence from the human growth hormone (hGH) gene. The hGH sequence serves to upregulate expression of the transgene and provides a polyadenylation signal. (See Sandgren, E.P., Luetteke, N.C., Palmiter, R. D., Brinster, R. L. & Lee, D. C. (1990), "Overexpression of TGF alpha in transgenic mice: Induction of epithelial hyperplasia, pancreatic metaplasia, and carcinoma of the breast," (*Cell* 61, 1121–1135).

The 5-kbp EcoR1 k14-NT-3-hGH fragment (FIG. 1a) was isolated on 0.8% Seaplaque agarose gel (FMC Corporation), extracted from the gel using glassmilk purification (Geneclean Bio 101), and run through a NACS column (Bethesda Research Laboratories).

The plasmid used to transfect mouse cells according to the present invention (K14-NT-3)-hGH has been deposited in *E. coli* with the American Type Culture Collection under the terms of the Budapest Treaty and is available as Accession No. [69889].

DNA was ethanol precipitated, resuspended in phosphate buffered saline at a concentration of 5 μg/ml, and injected into fertilized B6×C3 F1 hybrid mouse (Harlan Laboratory Supplies) embryos. Injections and implantations were carried out using standard procedures. (See Hogan, B., Costantini, F. & Lacy, E. (1986). *Manipulating the Mouse Embryo: A Laboratory Manual* (Cold Spring Harbor Press, Cold Spring Harbor, N.Y.).

Mice were screened for the transgene using Southern hybridization analysis on DNA extracted from tail and by slot blot hybridization. For Southern hybridizations, 10 μg of DNA was digested with BamH1, separated on an 0.7% agarose gel, transferred to nitrocellulose by blotting and probed with a random primed $^{32}$P-dCTP (New England Nuclear) labeled probe made to the full length NT-3 cDNA.

EXAMPLE 2

Analysis of mRNA expression by Northern hybridization. Northern analysis was performed on RNA that was isolated from various tissues using guanidium thiocyanate/phenol/chloroform extraction. (See Chomczynski, P. & Sacchi, N. (1987), "Single-step method of RNA isolation by acid guanidinium thiocyanate-phenol-chloroform extraction," *Analyt. Biochem.* 162, 156–159).

Ten micrograms of total RNA was resolved on a 1.2% agarose formaldehyde denaturing gel, transferred to Nytran membrane (Schleicher and Schuell) by blotting, baked 2 h at 80° C., and then hybridized to a $^{32}$P-dCTP labeled riboprobe made to the full length NT-3 cDNA.

EXAMPLE 3

In situ hybridization. $^{35}$S-labelled cRNA probes were generated by adding 1 μg of linearized to 2.5 mM each ATP, CTP, GTP, 15 mM [$^{35}$S]UTP (New England Nuclear) and either T7 or T3 polymerase (Stratagene) to generate antisense and sense probes, respectively. Incubation was for 60 min at 40° C. in transcription buffer containing 50 mM MgCl$_2$, 20 mM spermidine, 20 mM Tris (pH 7.4) and 10 mM DTT. The solution was phenol:chloroform extracted and precipitated with ammonium acetate and 2.5 volumes of ethanol in the presence of 25 μg carrier tRNA.

For in situ hybridization, tail skin was dissected, immediately frozen on dry ice, cryostated at 20 μm, mounted onto Glass plus slides and stored at −80° C. until hybridized. To hybridize, slides were brought to room temperature, fixed for 10 min in 4% paraformaldehyde, washed in diethyl pyrocarbonate (DEPC)-treated phosphate buffer, transferred to 0.25% acetic anhydride in 0.1M TEA (pH 8/0) for 10 min at room temperature, dehydrated through a graded series of alcohols and defatted in chloroform. Sections were hybridized for 12–24 hr at 60° C. in a hybridization solution consisting of 1×10$^7$ cpm/ml of $^{35}$S-labeled cRNA probe, 50% formamide, 1× Denhardt's solution, 200 mM Tris (pH 7.5), 10% dextran sulfate, 0.3 μg/ml salmon sperm DNA, 0.15 mg/ml tRNA, and 40 mM DTT. Slides were washed in 4×SSC (1×SSC=0.15M NaCl, 0.015M sodium citrate, pH 7.0), incubated in 20 mg/ml ribonuclease A (Sigma) dissolved in 10 mM Tris-saline, and then washed through descending concentrations of SSC. The final wash was with 0.1×SSC at 37° C. for 1 hour.

Sections were air-dried and placed in X-ray cassettes with Hyperfilm β-Max X-ray film (Amersham). Films were exposed for 3–7 days and developed in Kodak D-19. Selected slides were dipped in Kodak NTB-2 liquid emulsion, air-dried and exposed to film. Emulsion dipped slides were developed in D19, fixed in Kodak rapid fixer, counterstained with hematoxylin/eosin or cresyl violet and coverslipped in Permount.

Skin sections from transgenic mice and non-transgenic siblings were processed in parallel. Controls for probe specificity included hybridization using a sense cRNA probe and pretreatment of tissue with RNase. Both of these conditions resulted in the absence of hybridization.

EXAMPLE 4

Immunohistochemistry. Skin from mice typically between 4–6 months of age was analyzed. Mice were deeply anesthetized with Avertin and transcardially perfused with 4% paraformaldehyde in phosphate buffer. Tissue was removed and immersion fixed for at least 4 h, placed in 25% sucrose overnight, embedded in gelatin and cut at 40 μm thickness on a sliding microtome. Sections were blocked for 1 h in 5% normal goat serum (NGS), 2% bovine serum albumin (BSA), and 0.25% triton X-100 made in Tris buffered saline (100 mM Tris; 5 mM NaCl; pH 7.4) for 1 h, exposed overnight at room temperature to a primary antibody (anti-PGP 9.5, 1:5000; anti-NF150, 1:3000; dilutions made in 5% NGS and 0.25% triton), washed, and incubated in a 1:500 dilution of biotinylated goat anti-rabbit secondary for 1 h followed by a strep-avidin complex incubation (Vector Labs). Antibody binding was visualized using a nickel cobalt enhanced diaminobenzidine reaction.

Merkel cell and touch dome counting. To identify touch domes and Merkel cells associated with touch domes located on flank skin of adult mice skin was depilated and 24 h later mice were injected intraperitoneally with quinacrine (Sigma) (15 mg/kg; made in phosphate buffered saline), a fluorescent dye that concentrates in neuroendocrine cell types (14). 12–20 h following injection mice were deeply anesthetized and killed by cervical dislocation and flank skin removed. The skin was trimmed of connective tissue, mounted on a glass slike with a coverslip using glycerol, and Merkel cells associated with touch dome units counted using FITC fluorescence optics. The number of touch domes per cm$^2$ of flank skin was determined in a similar manner.

EXAMPLE 5

NT-3 may be used in the diagnosis and/or treatment of neurologic disorders, including, but not limited to, peripheral neuropathies, such as diabetic neuropathies, toxic and nutritional neuropathies, hereditary neuropathies, and AIDS related neuropathies, as well as degenerative diseases such as amyotrophic lateral sclerosis (ALS). It has been shown that NT-3 supports the survival of dopaminergic neurons. Accordingly, in a preferred embodiment, NT-3 may be used for the diagnosis of Parkinson's disease. Because NT-3 has been observed to exhibit a spectrum of activity different from brain derived neurotrophic growth factor (BDNGF) and nerve growth factor (NGF), NT-3 provides new and valuable options for inducing the regrowth and repair of the central nervous system.

The transgenic mice in accordance with the present invention, thus provide an in vivo model for testing drug interactions with neurons which are stimulated by NT-3. The K14-NT-3 mice are valuable to researchers that study the role of NT-3 in development and function of the adult nervous system. An area of intense study is the role of NT-3 in neurodegenerative disorders of the CNS and PNS. In addition, NT-3 has been shown to have antinociceptive effects (i.e., increase in tail-flick and hot plate response latency). Academic researchers as well as biotechnology companies are involved in such studies and would have interest in these mice as model systems in basic research studies as well as for applied studies such as drug testing.

To test the reaction and/or of drugs in treating neurodegenerative disorders, a drug candidate is administered to a mouse according to the invention. The behavioral effects and tissue changes of the mouse are determined upon administration of the drug.

References

1. K. M. Albers, D. E. Wright, B. M. Davis, *J. Neuroscience* 14, 1422 (1994).
2. T. P. Goodness, K. Albers, F. Davis, submitted.
3. L. C. Schecterson and M. Bothwell, *Neuron* 9, 449 (1992).
4. A. M. Davies, A. Horton, L. E. Burton, *J. Neurosci.* 13, 4961 (1993).
5. U. Arumae, U. Pirvola, J. Palgi, *J. Cell Biol.* 122, 1053 (1993).
6. R. M. Lindsay and A. J. Harmar, *Nature*, 337, 362 (1988).
7. R. W. Oppenheim, *Ann.Rev. Neurosci.* 14, 453 (1991).
8. C. Crowley, S. D. Spencer, M. C. Nishimura, *Cell* 76, 1001 (1994).
9. V. L. Buchman and A. M. Davies, *Development* 118, 989 (1993).
10. R. Vassar and E. Fuchs, *Genes and Develop.* 5, 714 (1991).
11. F. Pasche, Y. Merot, P. Carraux, *J. Invest. Derm.* 95, 247 (1990).
12. M. S. Airaksinen, M. Koltzenburg, G. R. Lewin, submitted.
13. K.-M. Gottschaldt and C. Vahle-Hinz, *Science* 214, 183 (1981).
14. C. A. Nurse and J. Diamond, Neuroscience 11, 509 (1984).
15. P. Ernfors, K.-F. Lee, J. Kucera, *Cell* 77, 503 (1994).
16. I. Farinas, K. R. Jones, C. Backus, *Nature* 369, 658 (1994).
17. S. O. Meakin and E. M. Shooter, *Trends Neurosci.* 15, 323 (1992).
18. N. Y. Ip, T. N. Stitt, P. Tapley, *Neuron* 100, 137 (1993).
19. V. M. K. Verge, J. P. Merlio, J. Grondin, *J. Neurosci.* 12, 4011 (1992).
20. M. Barbacid *J. Neurosci.* 25, 1386 (1994).
21. P. Ernfors, C. M. Rosario, J.-P. Merlio, *Mol. Brain Res.* 17, 217 (1993).
22. X. Mu, I. Silos-Santiago, S. L. Carroll, *J. Neurosci.* 13, 4029 (1993).
23. D. E. Wright and W. D. Snider, *J. Comp. Neurol.* 351, 329 (1995).
24. R. Levi-Montalcini, *Science* 237, 1154 (1987).
25. J. E. Dixon and D. McKinnon, *Dev. Brain Res.* 77, 177 (1994).
26. R. Klein, 1. Silos-Santiago, R. J. Smeyne, *Nature*, 368, 249 (1994).
27. C. A. Nurse, L. Macintyre, and J. Diamond, *Neuroscience* 11, 521 (1984).
28. G. D. Yancopoulos, P. C. Maisonpierre, N. Y. Ip, *Cold Spring Harbor Symposia on Quantitative Biology* 55, 371 (1990).
29. B. Hogan, F. Costantini, E. Lacy *Manipulating the Mouse Embryo: A Laboratory Manual* (Cold Spring Harbor Press, Cold Spring Harbor, N.Y., 1986).
30. R. D. Rose and D. Rohrlich, *J. Comp. Neurol.* 263, 365 (1987).

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A transgenic mouse whose somatic and germ cells contain and express an NT-3 transgene encoding mouse neurotrophic growth factor 3 (NT-3), wherein as a result of said expression, the peripheral nervous system of said mouse exhibits the following characteristics:

(a) NT-3 responsive neurons that are rescued from programmed cell death that normally occurs during the development of said mouse;

(b) an increase in sensory neurons that express trk C receptor relative to a mouse that does not express said NT-3 transgene; and (c) larger Merkel cell sensory units in the skin of said mouse than in the skin of a mouse that does not express said NT-3 transgene;

and further wherein said NT-3 transgene comprises a mouse NT-3 gene operatively linked at its 5' end to a human K14 keratin promoter and enhancer region and operatively linked at its 3' end to a contiguous 1.8 kbp region of the human growth hormone gene, said region comprising (1) an intron of the human growth hormone gene, and (2) a polyadenylation signal sequence.

2. The mouse of claim 1, wherein said mouse is fertile and capable of transmitting said NT-3 gene to its offspring.

3. The mouse of claim 1, wherein said NT-3 gene has been introduced into an ancestor of said mouse at an embryonic stage by microinjection.

4. The mouse of claim 1, wherein said human K14 keratin promoter and enhancer region is a 2.1 kbp sequence 5' upstream from the human K14 keratin gene.

5. The mouse of claim 1, wherein said NT-3 transgene is contained in a plasmid having American Type Culture Collection Accession No. 69889.

6. A method of testing the effect of a drug on the mouse of claim 1, comprising administering said drug to said mouse, and thereafter determining any behavioral effects and tissue changes in said mouse.

7. The method of claim 6, wherein said drug is a candidate for treatment of a neurodegenerative disorder.

* * * * *